US 6,558,696 B1

(12) United States Patent
Hille et al.

(10) Patent No.: US 6,558,696 B1
(45) Date of Patent: *May 6, 2003

(54) DESOXYPEGANINE

(75) Inventors: Thomas Hille, Neuwied (DE); Lothar Deurer, Koblenz (DE)

(73) Assignees: LTS Lohmann Therapie Systeme AG, Andernach (DE); HF Arzneimittelforschung, Werne (DE)

(*) Notice: Subject to any disclaimer, the term of this patent is extended or adjusted under 35 U.S.C. 154(b) by 0 days.

This patent is subject to a terminal disclaimer.

(21) Appl. No.: 09/889,943
(22) PCT Filed: Feb. 8, 2000
(86) PCT No.: PCT/EP00/00971
§ 371 (c)(1),
(2), (4) Date: Jul. 25, 2001
(87) PCT Pub. No.: WO00/48579
PCT Pub. Date: Aug. 24, 2000

(30) Foreign Application Priority Data

Feb. 19, 1999 (DE) .......................... 199 06 977

(51) Int. Cl.[7] .............. A61F 13/00; A61K 9/00; A61K 9/14; A01N 43/58; A01N 43/40; A01N 43/36; A01N 37/34
(52) U.S. Cl. .............. 424/449; 424/400; 424/484; 424/486; 424/487; 424/488; 514/250; 514/349; 514/408; 514/523
(58) Field of Search ............... 424/449, 400, 424/484, 486, 487, 488; 514/946, 964, 250, 349, 408, 523

(56) References Cited

U.S. PATENT DOCUMENTS 5,633,238 A * 5/1997 Snorrason .................... 514/80
5,700,480 A * 12/1997 Hille et al. .................. 424/448

FOREIGN PATENT DOCUMENTS

SU    1979-25213 B * 4/1978

OTHER PUBLICATIONS

Sadikova, et al., "Deoxypeganine injection solution," Chemical Abstracts, vol. 121, No. 8, Aug. 8, 1994 Columbus, Ohio, US (XP002140386).
Database WPI Section Ch, Week 197913 Derwent Publications Ltd, London, GB; Class B04, AN 1979-25213B (XP002140387).

* cited by examiner

Primary Examiner—Jose' G. Dees
Assistant Examiner—Sharmila S Gollamudi
(74) Attorney, Agent, or Firm—Frommer Lawrence & Haug LLP

(57) ABSTRACT

The invention relates to a transdermal therapeutic system (TTS) containing desoxypeganine (1,2,3,9-Tetrahydropyrrolo[2,1-b]quinazoline) as the active component, wherein the TSS includes a back layer impermeable to desoxypeganine and an adhesive reservoir layer that contains 10–80 weight percent polymeric material, 0.1–30 weight percent desoxypeganine and/or the pharmaceutically acceptable salts thereof and optionally a softening agent in proportions of 0.1–30 weight percent.

15 Claims, 2 Drawing Sheets

FIG. 2
In-Vitro release of deoxypeganine
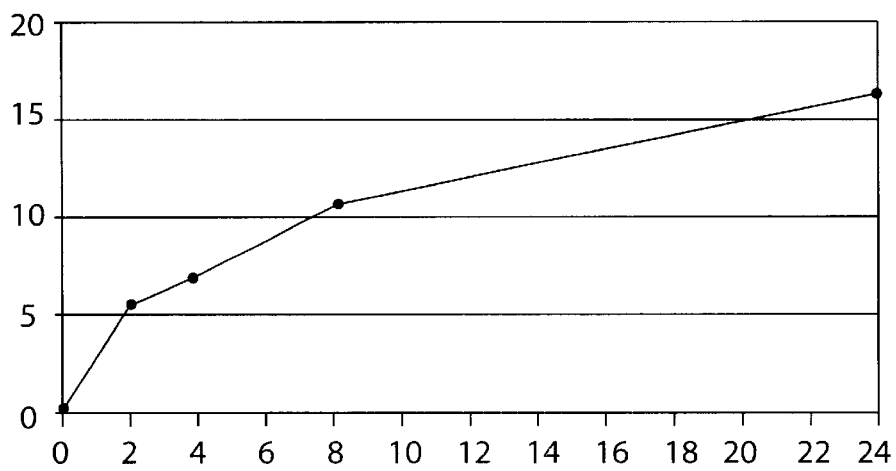
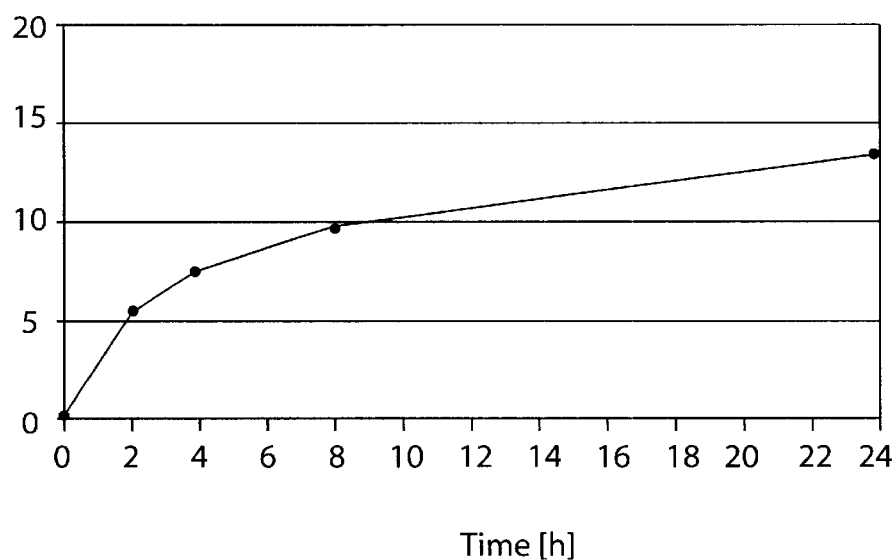

DESOXYPEGANINE

The invention relates to a transdermal therapeutic system (TTS) which contains desoxypeganine (1,2,3,9-tetrahydropyrrolo[2,1-b]quinazoline) as active constituent.

On account of its pharmacological properties, desoxypeganine belongs to the group of reversibly acting cholinesterase inhibitors. It is related in its actions to physostiginine, neostigmine and galanthamine, but also has specific properties. Desoxypeganine inhibits not only acetylcholinesterase, but also monoamine oxidase.

This advantage offsets its dose-related somewhat lower cholinesterase inhibitory action.

The therapy of Alzheimer's disease requires pharmaceutical forms which are long-acting and take account of the particular circumstances of this disease. Difficult therapy schemes or continuous infusions are not suitable for obvious reasons. Such a therapy within the meaning of the present invention is understood as meaning a medicinal treatment of dementias (in particular Alzheimer's dementia) which is used for influencing the mental capacity and/or for the treatment of concomitant symptoms.

What is more, a TTS is the pharmaceutical form of choice; nevertheless to date is has not been possible for desoxypeganine to be absorbed transdermally in the necessary amount.

The object of the invention is therefore the provision of desoxypeganine and/or one of its pharmaceutically tolerable salts in the form of a transdermal therapeutic system which releases desoxypeganine and/or its pharmaceutically tolerable salt in a controlled manner over a period of at least 24 hours and guarantees that the desoxypeganine does not noticeably decompose during the storage of the prefabricated transdermal therapeutic system and ensures that the desoxypeganine penetrates through human skin to the required extent in vivo.

BRIEF DESCRIPTION OF THE DRAWINGS

FIG. 2 depicts the in-vitro release of desoxypeganine using the formulations of Examples 1 and 2.

Figure 1:
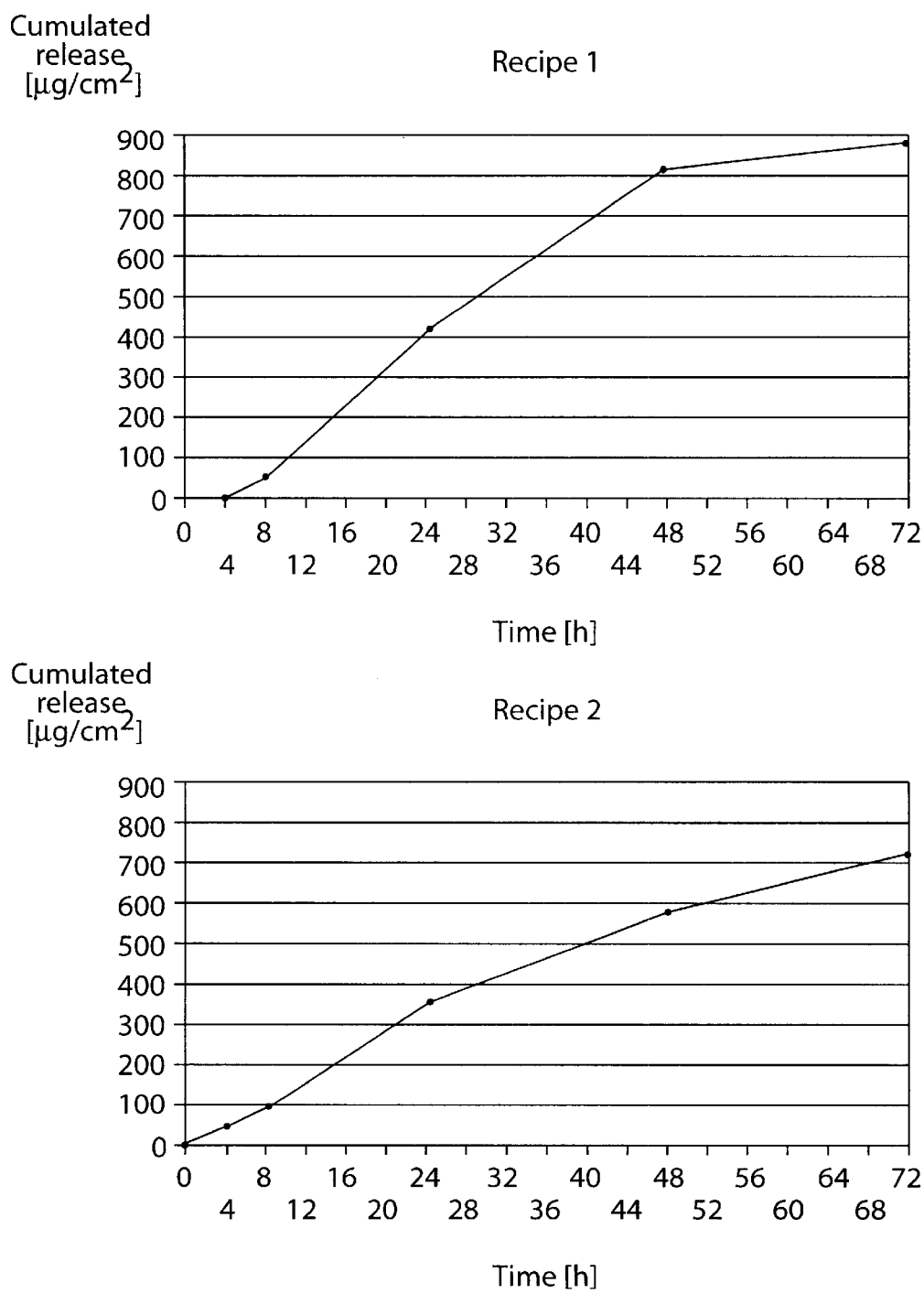
FIG. 1 depicts the release of desoxypeganine through the human skin using the formulations of Examples 1 and 2.

This object is surprisingly achieved with the invention by means of a transdermal therapeutic system which comprises a back layer which is impermeable to desoxypeganine or one of its pharmaceutically tolerable salts and a contact-adhesive reservoir layer. This reservoir layer comprises 10–80% by weight of polymer material, 0.1–30% by weight of desoxypeganine and/or one of its pharmaceutically tolerable salts and, if appropriate, a plasticizer in amounts of 0.1%–30% by weight.

Features of further advantageous embodiments of a transdermal therapeutic system according to the invention are described in detail.

This achievement is all the more surprising, as desoxypeganine is structurally assigned to the tricyclic systems. Tricyclic systems are a class of substance which is considered as being able to penetrate the human skin only to an inadequate extent.

Without restricting the scope of the invention, pharmaceutically tolerable salts of desoxypeganine are preferably understood as meaning its hydrobromide and hydrochloride.

The active-compound-impermeable back layer can consist of flexible or inflexible material. Substances which can be used for its preparation are polymer films or metal foils, such as aluminum foil, which are used on their own or coated with a polymeric substrate.

Textile fabrics can also be used if the constituents of the reservoir cannot penetrate them on account of their physical composition. In a preferred embodiment, the back layer is a laminate of a foil which is vapor-coated with aluminum.

The reservoir layer consists of a polymer matrix and the active compound, the polymer matrix guaranteeing the cohesion of the system. It consists of a base polymer and, if appropriate, the customary additives. The selection of the base polymer depends on the chemical and physical properties of the deoxypeganine. Exemplary base polymers are rubber, rubber-like, synthetic homo-, co- or block polymers, polyacrylic acid esters and their copolymers, polyurethanes and silicones. Fundamentally, all polymers are suitable which can be employed in the preparation of contact adhesives and are physiologically acceptable. Those which consist of block copolymers based on styrene and 1,3-dienes, polyisobutylenes, silicones, polymers based on acrylate and/or methacrylate are particularly preferred.

Of the block copolymers based on styrene and 1,3-dienes, linear styrene/isoprene or styrene/butadiene block copolymers are very particularly employed.

Preferred polymers based on acrylate are self-crosslinking acrylate copolymers of 2-ethylhexyl acrylate, vinyl acetate and acrylic acid with or non self-crosslinking acrylate copolymers without titanium chelate ester.

Suitable polymers which can be added to the base polymer are polymethacrylates and polyvinyls. Preferred methacrylates are copolymers based on dimethylaminoethyl methacrylates and neutral methacrylic acid esters. Polyvinyls preferably employed are polyvinylpyrrolidones and polyvinyl alcohols.

Cellulose derivatives have proven particularly advantageous as constituents of the polymer material.

The choice of the plasticizer depends on the polymer. Higher alcohols such as dodecanol, undecanol, octanol, oleyl alcohol and 2-octyldodecanol, esters of carboxylic acids (e.g. isopropyl myristate) are particularly suitable, where the alcohol component can also be a polyethoxylated alcohol, diesters of dicarboxylic acids, e.g. di-n-butyl adipate, and triglycerides, in particular medium-chain triglycerides of the caprylic/capric acids of coconut oil. Further examples of a suitable plasticizer are polyhydric alcohols, e.g. glycerol and propane-1,2-diol among others, which can also be etherified by polyethylene glycols.

Suitable penetration promoters which can be employed in a further embodiment of the transdermal therapeutic system according to the invention are all carboxylic acids which are physiologically acceptable. Octanoic acid, levulinic acid, lauric acid, undecenoic acid, oleic acid and stearic acid and their isomers are particularly suitable.

The nature of the customary additives used in further embodiments depends on the polymer employed: according to their function, they can be divided into, for example, tackifiers, stabilizers, excipients and fillers. The physiologically acceptable substances suitable for this are known to the person skilled in the art.

The reservoir layer has an intrinsic tackiness such that an intimate contact with the skin of the patient during the administration period of the TTS according to the invention is ensured.

A removable protective layer which is in contact with the reservoir layer and is removed before use consists, for example, of the same materials as are used for the production of the back layer provided that they are made removable, such as, for example, by a silicone treatment.

Other removable protective layers are, for example, polytetrafluoroethylene, treated paper, cellophane, polyvinyl chloride and the like. If the laminate according to the invention is divided into shapes conforming with therapy (patches) before application of the protective layer, the protective layer shapes to be applied can then have a projecting end, with whose aid they can be peeled off more easily from the patch.

In further embodiments according to the invention, the reservoir layer can also be covered by a membrane controlling the release of the desoxypeganine and/or one of its pharmaceutically tolerable salts, e.g., microporous or semipermeable membrane. If this membrane is not contact-adhesive, a further contact-adhesive layer can ensure the skin contact.

The transdermal therapeutic system according to the invention is produced by homogeneously mixing the active compound together with the constituents of the contact-adhesive reservoir layer, if appropriate in solution, and spreading it onto the active-compound-impermeable back layer, whereupon the solvent(s) is/are optionally removed. The adhesive layer is then provided with an appropriate protective layer, if appropriate after a membrane controlling the release rate has been bonded it.

The reverse route, in that the adhesive solution is spread onto the protective layer, is also fundamentally possible. The solvent is also removed in this case and the protective layer is then covered with the back layer.

The invention is illustrated by the following examples:

EXAMPLE 1

1.0 g of lauric acid and 0.5 g of isopropyl myristate are mixed with stirring. 1.0 g of desoxypeganine is then introduced; the mixture is stirred until the solid has dissolved completely (approx. 30 min. visual checking). 1.625 g of ethylcellulose, dissolved in 6.25 g of ethyl acetate, are then added with stirring; the mixture is homogenized. 4.5 g of Abitol and 1.25 g of Hercures C, dissolved in 1.25 g of gasoline, are then additionally added with stirring. The mixture is stirred at room temperature for 3 hours. The loss by evaporation is compensated.

17.375 g of a 56.82% strength (w/w) active compound-containing adhesive solution results, which is coated onto an aluminized and siliconized polyethylene film using a 350 $\mu$m doctor blade. After the solvent has been removed by drying at 60° C. for 30 minutes, the adhesive film is covered with a 15 $\mu$m polyester film. Using suitable cutting tools, an area of 16 $cm^2$ is punched out and the borders are removed by squaring-off (removal of excess matrix parts). The release of this and the other recipe examples is represented in the figures; both the controlled release into a physiological saline solution and that through human skin are shown there.

EXAMPLE 2

The TTS of this example is fabricated according to the scheme indicated in Example 1, but without use of lauric acid. The recipe constituents after drying are shown in the following table.

Desoxypeganine Recipes

| Material employed | Experiment 1, content (%) | Experiment 2; content (%) |
|---|---|---|
| Ethyl acetate | — | — |
| Gasoline | — | — |
| Isopropyl myristate | 5.06 | 5.06 |
| Hercures C | 12.66 | 13.92 |
| Abitol | 45.57 | 50.63 |
| Desoxypeganine | 10.12 | 10.12 |
| Ethyl cellulose | 16.45 | 20.25 |
| Lauric acid | 10.12 | — |

The in-vitro release was determined at 37° C. in a shaking water bath. The acceptor medium was 100 ml of physiological saline solution, which was completely replaced after 2, 4 and 8 hours. The concentration was determined by HPLC after 2, 4 and 8 and 24 hours. The penetration in the human skin was measured in Franz's diffusion cells.

What is claimed is:

1. A transdermal therapeutic system (TTS) for the administration of desoxypeganine and/or its pharmaceutically acceptable salts to the skin, having an active-compound-impermeable backing layer and a contact-adhesive reservoir layer, wherein the reservoir layer comprises 10–80% by weight of polymer material and 0.1–30% by weight of desoxypeganine and/or one of its pharmaceutically acceptable salts.

2. The TTS as claimed in claim 1, which further comprises a semipermeable or microporous membrane for controlling the release of desoxypeganine and/or its pharmaceutically acceptable salts.

3. The TTS as claimed in claim 1, wherein the contact-adhesive reservoir layer further comprises 0.1–30% by weight of a penetration promoter.

4. The TTS as claimed in claim 3, wherein the penetration promoter is a carboxylic acid.

5. The TTS as claimed in claim 1, wherein the contact-adhesive reservoir layer further comprises 0.1–30% by weight of a plasticizer.

6. The TTS as claimed in claim 1, wherein the polymer material is polyacrylates, which are the polymerization products of at least one member selected from the group consisting of acrylic acid, acrylic acid esters, methacrylic acid, and methacrylic acid esters.

7. The TTS as claimed in claim 6, wherein the polymer material is the polymerization product of esters of acrylic acid which, as alcoholic components, comprise straight-chain or branched alcohols having 4–10 carbon atoms.

8. The TTS as claimed in claim 6, wherein the polymer material is the polymerization product of esters of acrylic acid which, as alcoholic components, comprise straight-chain or branched alcohols having 2–4 carbon atoms.

9. The TTS as claimed in claim 6, wherein the polymer material is the polymerization product of esters of methacrylic acid which, as alcoholic components, comprise aminoalcohols.

10. The TTS as claimed in claim 1, wherein the polymer material comprises self crosslinking or non self-crosslinking acrylate copolymers.

11. The TTS as claimed in claim 1, which further comprises a removable protective layer that is removed prior to use.

12. The TTS as claimed in claim 1, wherein the polymer material comprises cellulose and its derivatives.

13. A method for treating dementia in a patient in need thereof which comprises applying the contact-adhesive reservoir layer of the TTS according to claim 1, to the skin of the patient for a period of time and administering the desoxypeganine and/or its pharmaceutically acceptable salts in a controlled manner.

14. A method according to claim 13, wherein said dementia is Alzheimer's disease.

15. A method according to claim 13, wherein the period of time is a period of at least 24 hours.

\* \* \* \* \*